(12) United States Patent
Izumi et al.

(10) Patent No.: US 10,905,117 B2
(45) Date of Patent: Feb. 2, 2021

(54) ANTIMICROBIAL AGENT CONTAINING POLYALKYLENEIMINE DERIVATIVE

(71) Applicant: NIPPON SHOKUBAI CO., LTD, Osaka (JP)

(72) Inventors: Hiroko Izumi, Ibaraki (JP); Masahiro Nakanosho, Ibaraki (JP)

(73) Assignee: NIPPON SHOKUBAI CO., LTD, Osaka (JP)

( * ) Notice: Subject to any disclaimer, the term of this patent is extended or adjusted under 35 U.S.C. 154(b) by 22 days.

(21) Appl. No.: 15/509,094

(22) PCT Filed: Sep. 10, 2015

(86) PCT No.: PCT/JP2015/075756
§ 371 (c)(1),
(2) Date: Mar. 6, 2017

(87) PCT Pub. No.: WO2016/039425
PCT Pub. Date: Mar. 17, 2016

(65) Prior Publication Data
US 2017/0258082 A1    Sep. 14, 2017

(30) Foreign Application Priority Data

Sep. 10, 2014  (JP) ................................ 2014-184692
Dec. 5, 2014   (JP) ................................ 2014-247311
Mar. 12, 2015  (JP) ................................ 2015-049989

(51) Int. Cl.
| | | |
|---|---|---|
| *A01N 33/08* | (2006.01) | |
| *A01N 61/00* | (2006.01) | |
| *A61K 8/19* | (2006.01) | |
| *A61K 8/365* | (2006.01) | |
| *A61K 8/41* | (2006.01) | |
| *A61K 8/46* | (2006.01) | |
| *A61K 8/84* | (2006.01) | |
| *A61K 8/86* | (2006.01) | |
| *A61Q 15/00* | (2006.01) | |
| *A61Q 17/00* | (2006.01) | |
| *C08G 73/02* | (2006.01) | |
| *C11D 1/22* | (2006.01) | |
| *C11D 3/37* | (2006.01) | |
| *C11D 3/48* | (2006.01) | |
| *A61Q 5/00* | (2006.01) | |

(52) U.S. Cl.
CPC ............. *A01N 33/08* (2013.01); *A01N 61/00* (2013.01); *A61K 8/19* (2013.01); *A61K 8/365* (2013.01); *A61K 8/41* (2013.01); *A61K 8/463* (2013.01); *A61K 8/84* (2013.01); *A61K 8/86* (2013.01); *A61Q 5/006* (2013.01); *A61Q 15/00* (2013.01); *A61Q 17/005* (2013.01); *C08G 73/0206* (2013.01); *C11D 1/22* (2013.01); *C11D 3/3723* (2013.01); *C11D 3/48* (2013.01); *A61K 2800/5424* (2013.01); *A61K 2800/594* (2013.01); *A61K 2800/596* (2013.01)

(58) Field of Classification Search
CPC .......... A01N 33/08; A01N 61/00; A61K 8/19; A61K 8/365; A61K 8/41; A61K 8/463; A61K 8/84; A61K 8/86; A61K 2800/5424; A61K 2800/594; A61K 2800/596; A61Q 15/00; A61Q 17/005; A61Q 5/006; C08G 73/0206; C11D 1/22; C11D 3/3723; C11D 3/48
See application file for complete search history.

(56) References Cited

U.S. PATENT DOCUMENTS

| | | | |
|---|---|---|---|
| 2005/0085404 A1 | 4/2005 | Yoneda et al. | |
| 2007/0231291 A1 | 10/2007 | Huang et al. | |
| 2010/0111881 A1 | 5/2010 | Huang et al. | |
| 2011/0180755 A1* | 7/2011 | Adachi | C08F 8/32 252/194 |
| 2011/0318280 A1 | 12/2011 | Huang et al. | |

FOREIGN PATENT DOCUMENTS

| | | |
|---|---|---|
| JP | 19855135585 | 7/1985 |
| JP | 1986064325 | 4/1986 |
| JP | 1997012717 | 1/1997 |
| JP | 1997157113 | 6/1997 |
| JP | 2000062096 | 2/2000 |

(Continued)

OTHER PUBLICATIONS

International Search Report, PCT/JP2015/075756, dated Dec. 28, 2015.
Lin J, Qiu S, Lewis K, Klibanov AM, Biotechnol. Prog., 18(5), 1082-1086 (2002).
Falczak et al., Antimicrobial activity of poly propylene imine dendrimers, New J. Chem., 2012, 36, 2215-2222.
Extended European Search Report, dated Jan. 25, 2018.
Official Notice of Reason for Refusal, Japanese.

(Continued)

*Primary Examiner* — Matthew P Coughlin
*Assistant Examiner* — Thurman Wheeler
(74) *Attorney, Agent, or Firm* — Porzio Bromberg & Newman P.C.

(57) ABSTRACT

The present invention is an antimicrobial agent containing a polyalkyleneimine derivative formed by adding a substituent group having a structure of a following Formula (1) to a nitrogen atom of polyalkyleneimine.

$$-CH_2CH(OH)CH_2-O-R^1 \quad (1)$$

In the formula, $R^1$ represents an alkyl group with 6 to 20 carbon atoms, an alkenyl group with 6 to 20 carbon atoms, an aryl group with 6 to 20 carbon atoms, or $-(CH_2CH_2O)_n-R^2$. $R^2$ represents an alkyl group with 6 to 20 carbon atoms, an alkenyl group with 6 to 20 carbon atoms, or an aryl group with 6 to 20 carbon atoms. n represents an integer of 1 to 50.

6 Claims, No Drawings

(56) References Cited

FOREIGN PATENT DOCUMENTS

| | | |
|---|---|---|
| JP | 2005170977 A | 6/2005 |
| JP | 2005350640 A | 12/2005 |
| JP | 2009161762 | 7/2009 |

OTHER PUBLICATIONS

Kao hygiene solution, the KAO Corporation C&S operation division, Jul. 15, 2004, No. 7, p. 24-25 (partial translation).
Japanese Industrial Standard; JIS L1902: 2008, Testing for anitbacterial activity and efficacy on textile products; Published in English 2009.
Communication Pursuant to Article 94(3) EPC dated Jun. 4, 2019.

\* cited by examiner

ANTIMICROBIAL AGENT CONTAINING POLYALKYLENEIMINE DERIVATIVE

TECHNICAL FIELD

The present invention relates to a polymer type antimicrobial agent using polyalkyleneimine derivative with specific structure. More specifically, the present invention relates to an antimicrobial agent using polyalkyleneimine derivative, which is a polyalkyleneimine derivative introduced with a hydrophobic group and has a hydroxyl group and an ether group between a nitrogen atom and a hydrophobic group.

BACKGROUND ART

In recent years, due to higher attention to cleanliness or hygiene, an antimicrobial agent is used in various fields including cleaning agents, cosmetics, paints, resins, and molded articles. The antimicrobial agent is required to have safety as well as antimicrobial performance. Since a polymer type antimicrobial agent has no volatile property and is hardly eluted, it has low toxicity to humans. From such point of view, it receives attention as an antimicrobial agent having high safety.

The polymer type antimicrobial agent is referred to exhibit its function by disrupting cell membrane of a cell. It is considered that the method of attacking a cell membrane as a target is very unlikely to have an occurrence of resistant microbes when compared to a conventional microbial agent which attacks a specific protein as a target.

As a polymer type antimicrobial agent, an antimicrobial agent in which a hydrophobic group is introduced to polyalkyleneimine has been conventionally known. In Patent Literature 1, an antimicrobial agent where polyethyleneimine introduced with at least one hydrophobic group selected from an alkyl group, an acyl group, and a hydroxyalkyl group is neutralized with acid, is described. In Patent Literature 2, an antimicrobial agent as a combination of polyethyleneimine introduced with a hydrophobic group and a carboxy group, and silver, zinc, and copper is described.

In Patent Literature 3, an antimicrobial agent of polyalkyleneimine derivative introduced with a hydrophobic group is also described. In Non-Patent Literature 1, an antimicrobial agent in which an alkyl group is introduced to glass-immobilized polyethyleneimine is described.

CITATION LIST

Patent Literatures

Patent Literature 1: JP H09-157113 A
Patent Literature 2: JP H09-12717 A
Patent Literature 3: JP 2009-524719 A (corresponding to US Patent Application Publication No. 2007/231291)

Non-Patent Literatures

Non-Patent Literature 1: Lin J, Qiu S, Lewis K, Klibanov AM, Biotechnol. Prog., 18 (5), 1082-1086 (2002)

SUMMARY OF INVENTION

Technical Problem

According to Patent Literatures 1 and 2, however, only the polyethyleneimine introduced with a hydrophobic group is not enough to exhibit an antimicrobial performance. As such, it is necessary to have acid neutralization or addition of an inorganic compound such as silver, zinc, or copper. As the antimicrobial agent is used after being added to various kinds of product such as cleaning agents, cosmetics, paints, resins, or molded articles, it has an optimum pH range for its production or use. Furthermore, various additives like chelating agent required for other performances are blended therein. According to the antimicrobial agent of Patent Literatures 1 and 2, there is a possibility that the antimicrobial performance is impaired under the influence of conditions for production and/or use of a product.

A part of the antimicrobial agent described in Patent Literature 3 has a quaternary ammonium salt structure. Furthermore, the antimicrobial agent introduced only with the alkyl group described in Non-Patent Literature 1 has a low antimicrobial property, and thus a methyl group is additionally added for quaternization to have an improved antimicrobial property. However, the quaternary ammonium salt type antimicrobial agent has poor stability under alkali conditions, and also it is easily affected by an anionic compound like an anionic surfactant.

As described above, many of the polymer type antimicrobial agents have high safety but low antimicrobial performance, and in particular, from the viewpoint of the immediate effectiveness, there are many agents inferior to a low molecular antimicrobial agent.

Thus, the present invention is made in view of the aforementioned problems of conventional techniques, and an object of the present invention is to provide a polymer type antimicrobial agent which has high antimicrobial performance, in particular, excellent immediate effectiveness, and is suitable for application to various product forms.

Solution to Problems

The inventors of the present invention conducted intensive studies to solve the problems described above. As a result, they found that the problems can be solved by introducing a hydrophobic group to the nitrogen atom of polyalkyleneimine and placing a hydroxyl group and an ether group between the nitrogen atom and hydrophobic group, and they completed the present invention accordingly.

Namely, one aspect of the present invention is an antimicrobial agent using a polyalkyleneimine derivative introduced with a hydrophobic group, and the object is achieved by the antimicrobial agent comprising a polyalkyleneimine derivative which is obtained by adding substituent group having a hydrophobic group with the structure of the following Formula (1) to the nitrogen atom of polyalkyleneimine.

[Chemical Formula 1]

$$-CH_2CH(OH)CH_2-O-R^1 \qquad (1)$$

In the formula, $R^1$ represents an alkyl group with 6 to 20 carbon atoms, an alkenyl group with 6 to 20 carbon atoms, an aryl group with 6 to 20 carbon atoms, or $-(CH_2CH_2O)_n-R^2$. $R^2$ represents an alkyl group with 6 to 20 carbon atoms, an alkenyl group with 6 to 20 carbon atoms, or an aryl group with 6 to 20 carbon atoms. n represents an integer of 1 to 50.

Furthermore, according to another aspect of the present invention, a personal care product, a product for caring household goods, or a skin care product including the antimicrobial agent described above is provided.

DESCRIPTION OF EMBODIMENTS

Hereinbelow, embodiments to carry out the present invention are explained. However, the present invention is not limited to those embodiments.

Meanwhile, in the specification, "X to Y" representing a range means "X or more and Y or less". Furthermore, unless specifically described otherwise, operations and measurements of physical properties or the like are carried out at conditions of room temperature (20 to 25° C.)/relative humidity of 40 to 50%.

The present invention provides an antimicrobial agent containing a polyalkyleneimine derivative that is obtained by adding a substituent group with the structure of the following Formula (1) to the nitrogen atom of polyalkyleneimine. Meanwhile, in the specification, the polyalkyleneimine derivative that is obtained by adding a substituent group with the structure of the following Formula (1) to the nitrogen atom of polyalkyleneimine is also simply referred to as a "polyalkyleneimine derivative" or a "polyalkyleneimine derivative according to the present invention."
[Chemical Formula 2]

In the formula, $R^1$ represents an alkyl group with 6 to 20 carbon atoms, an alkenyl group with 6 to 20 carbon atoms, an aryl group with 6 to 20 carbon atoms, or —$(CH_2CH_2O)_n$—$R^2$. $R^2$ represents an alkyl group with 6 to 20 carbon atoms, an alkenyl group with 6 to 20 carbon atoms, or an aryl group with 6 to 20 carbon atoms. n represents an integer of 1 to 50.

The polyalkyleneimine derivative according to the present invention is characterized in that a hydrophobic group (that is, $R^1$ in the above Formula (1)) is introduced to the nitrogen atom of polyalkyleneimine and a hydroxyl group and an ether group are present between the nitrogen atom of polyalkyleneimine and the hydrophobic group. The action mechanism of the polyalkyleneimine derivative according to the present invention is considered to be the same as the action mechanism of an antimicrobial peptide like Magainin-2, in which the amino group derived from the nitrogen atom is adsorbed to a negatively charged cell membrane based on an electrostatic interaction, the polymer (polyalkyleneimine derivative) penetrate the cell membrane, and the cell membrane is disrupted by a hydrophobic group. To have more efficient operation of this action mechanism, the balance between the hydrophilic group (—$CH_2CH(OH)CH_2$— part in the Formula (1)) and the hydrophobic group ($R^1$ part in the above Formula (1)) is important. If an ether group is present between the amino group and hydrophobic group, the hydrophobic group can freely move via the oxygen atom. For such reasons, the hydrophobic group can more easily approach the surface of a cell membrane compared to a polyalkyleneimine derivative having no ether group present between the amino group (that is, nitrogen atom) and hydrophobic group, and the polyalkyleneimine derivative according to the present invention can disrupt a cell membrane more efficiently. Therefore, according to the polyalkyleneimine derivative of the present invention, the antimicrobial property can significantly be enhanced. Furthermore, according to the polyalkyleneimine derivative of the present invention, penetration of the polymer to inside of a cell membrane or activity of disrupting a cell membrane by a hydrophobic group is promoted so that the antimicrobial performance is enhanced, and in particular, excellent immediate effectivity is obtained.

Furthermore, by using an amine (primary, secondary, or tertiary), there is no problem of having decomposition even at alkali conditions, and thus the stability is high. Furthermore, even in the presence of an anionic compound such as an anionic surfactant, the antimicrobial property is maintained.

Thus, according to the present invention, it is possible to provide a polymer type antimicrobial agent having high antimicrobial performance, in particular, excellent immediate effectiveness. Furthermore, the antimicrobial agent of the present invention can be applied to various product forms including cleaning agent, cosmetics, paints, resins, and molded articles.

Meanwhile, the aforementioned action mechanism is just an assumption, and the present invention is not limited to the above action mechanism.

In the present invention, the "antimicrobial agent" indicates an agent with antimicrobial performance. The antimicrobial performance means having any one of bactericidal (killing microbes) performance and bacteriostatic (suppressing growth of microbe) performance, and the microbes as an object include bacteria and fungi.

Examples of the bacteria include Gram negative bacteria such as *Escherichia coli*, *Pseudomonas aeruginosa*, *Salmonella* like *Salmonella choleraesuis*, *Moraxella* like *Moraxella osloensis*, or *Legionella* like *Legionella pneumophila*, and Gram positive bacteria such as *Staphylococcus aureus*, *Corynebacterium xerosis*, and *Clostridium* bacteria. Examples of the fungi include *Malassezia* fungus like *Malassezia furfur*, *Candida* fungus like *Candida albicans*, yeasts such as *Rhodotorula* yeast like *Rhodotorula rubra* or bread yeast like *Saccharomyces cerevisiae*, and fungi such as *Aspergillus* fungus like *Aspergillus niger*, Red mold like genus *Fusarium*, and Black mold like *Cladosporium cladosporioides*. In particular, as the Gram negative bacteria have an outer membrane and an inner membrane in a cell membrane, it is difficult to have exhibition of an antimicrobial performance for them. Accordingly, an antimicrobial agent effective for the Gram negative bacteria is desirable.

The polyalkyleneimine in the polyalkyleneimine derivative introduced with a hydrophobic group according to the present invention is introduced indicates a polymer which has a repeating unit of which main chain consists of an alkylene group and an amino group and has a repeating unit with the structure of the following Formula (A) and/or the Formula (B).

[Chemical Formula 3]

In the above Formula (A) and the Formula (B), Q represents an alkylene group. Herein, examples of the alkylene group represented by Q include an ethylene group, a propylene group, and a butylenes group. The alkylene group may be a single type or two or more kinds. In particular, the alkylene group is preferably an ethylene group. Namely, the polyalkyleneimine is preferably polyethyleneimine.

$R^1$ as a hydrophobic group in the substituent group having the structure of the above Formula (1) represents an alkyl group with 6 to 20 carbon atoms, an alkenyl group with 6 to 20 carbon atoms, an aryl group with 6 to 20 carbon atoms, or —(CH$_2$CH$_2$O)$_n$—R$^2$. With regard to the substituent group of the formula —(CH$_2$CH$_2$O)$_n$—R$^2$; R$^2$ represents an alkyl group with 6 to 20 carbon atoms, an alkenyl group with 6 to 20 carbon atoms, or an aryl group with 6 to 20 carbon atoms. n represents an integer of 1 to 50. Considering the further improved antimicrobial property, n is preferably 1 to 20. By having such hydrophobic group, good balance between hydrophobicity and hydrophilicity is obtained, and as the penetration to the inside of a cell wall is improved without compromising the mobility of the molecule, the antimicrobial performance is enhanced. Herein, when the carbon atom number of the alkyl group or alkenyl group, or the alkyl group or alkenyl group in the substituent group of —(CH$_2$CH$_2$O)$_n$—R$^2$ is 5 or less, a sufficient antimicrobial property is not exhibited in spite of improved hydrophilicity (that is, more easily soluble in water). On the other hand, when the carbon atom number of the alkyl group or alkenyl group, or the alkyl group or alkenyl group in the substituent group of —(CH$_2$CH$_2$O)$_n$—R$^2$ is 21 or more, it is difficult to get dissolved in water so that the agent cannot sufficiently act against microbes that are mainly present in an aqueous system. Furthermore, as the antimicrobial property is lowered on the contrary to above, the antimicrobial property cannot be sufficiently exhibited.

Herein, the alkyl group with 6 to 20 carbon atoms is not particularly limited, and it may be a linear or branched alkyl group with 6 to 20 carbon atoms. Specific examples thereof include a hexyl group, an isohexyl group, a heptyl group, an octyl group, a nonyl group, a decyl group, a undecyl group, a dodecyl group (lauryl group), a 2-ethylhexyl group, a tridecyl group, a tetradecyl group, a pentadecyl group, a hexadecyl group, a heptadecyl group, an octadecyl group, a nonadecyl group, and an eicosyl group.

The alkenyl group with 6 to 20 carbon atoms is not particularly limited, and it may be a linear or branched alkenyl group with 6 to 20 carbon atoms. Specific examples thereof include a 1-hexenyl group, a 2-hexenyl group, a 3-hexenyl group, a 1-heptenyl group, a 2-heptenyl group, and a 3-heptenyl group.

The aryl group with 6 to 20 carbon atoms is not particularly limited, and examples thereof include a phenyl group, a benzyl group, a phenethyl group, an o-, m- or p-tolyl group, a 2,3- or 2,4-xylyl group, a mesityl group, a naphthyl group, an anthryl group, a phenanthryl group, a biphenylyl group, a benzhydryl group, a trityl group, and a pyrenyl group.

Among them, an alkyl group with 6 to 16 carbon atoms is preferable. An alkyl group with 6 to 12 carbon atoms is more preferable. An alkyl group with 6 to 10 carbon atoms is even more preferable, and an alkyl group with 6 to 8 carbon atoms is particularly preferable. As for $R^2$, an alkyl group with 6 to 16 carbon atoms is preferable, and an alkyl group with 6 to 12 carbon atoms is more preferable. If the carbon atom number of $R^1$ and $R^2$ is 16 or less, the hydrophilicity or the molecular mobility is further enhanced so that the penetration to the inside a cell membrane or the antimicrobial performance can be further improved.

A ratio for introducing the substituent group having a structure of the above Formula (1) to the nitrogen atom of polyalkyleneimine is preferably 5% by mol or more, more preferably 10% by mol or more, and particularly preferably 12% by mol or more of the total nitrogen atoms. Furthermore, it is preferably 70% by mol or less, more preferably 60% by mol or less, even more preferably 50% by mol or less, and particularly preferably 30% by mol or less. When the ratio is within this range, the effect of a hydrophobic group to disrupt a cell membrane is shown at sufficient level so that high antimicrobial performance is obtained. Furthermore, when the ratio for introducing the substituent group is 30% by mol or less, excellent solubility in water is obtained.

The antimicrobial performance, persistence of the antimicrobial performance and safety of the polyalkyleneimine derivative of the present invention to which a hydrophobic group is introduced varies depending on number average molecular weight (Mn) of the polyalkyleneimine which is a raw material. A number average molecular weight (Mn) of the polyalkyleneimine which is a raw material is preferably 300 or higher, more preferably 500 or higher, and particularly preferably 600 or higher. Furthermore, the upper limit of the number average molecular weight is, although not particularly limited, preferably 100,000 or lower, more preferably 70,000 or lower, even more preferably 10,000 or lower, still even more preferably 5,000 or lower, and particularly preferably 3,000 or lower. By having such number average molecular weight, high antimicrobial performance can be exhibited with low skin irritation or toxicity to humans. The number average molecular weight is obtained by GPC (gel permeation chromatography), ebullioscopy, or the like. In the present specification, values measured by ebullioscopy are taken as the number average molecular weight.

A weight average molecular weight (Mw) of the polyalkyleneimine which is a raw material is preferably 400 or higher, and more preferably 500 or higher from the viewpoint of the antimicrobial performance, persistence of the antimicrobial performance and safety. Furthermore, the upper limit of the weight average molecular weight is preferably 70,000 or lower, more preferably 10,000 or lower, even more preferably 5,000 or lower, and particularly preferably 3,000 or lower. The weight average molecular weight is obtained by the GPC method, and specifically, the values that are measured by the method described in Examples are used.

The polyalkyleneimine derivative of the present invention to which a hydrophobic group is introduced is obtained by an addition reaction of polyalkyleneimine with glycidyl ether of the following Formula (2). Glycidyl ether is also used as a raw material of an epoxy resin or the like, and it is also preferable due to easy industrial obtain ability.

[Chemical Formula 4]

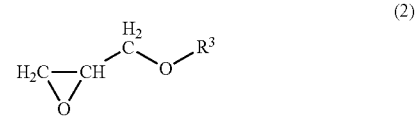

(2)

In the formula, $R^3$ represents an alkyl group with 6 to 20 carbon atoms, an alkenyl group with 6 to 20 carbon atoms, an aryl group with 6 to 20 carbon atoms, or —(CH$_2$CH$_2$O)$_m$—R$^4$. $R^4$ represents an alkyl group with 6 to 20 carbon atoms, an alkenyl group with 6 to 20 carbon atoms, or an aryl group with 6 to 20 carbon atoms. m represents an integer of 1 to 50.

A preferred form of $R^3$ and $R^4$ in the above Formula (2) is the same as the form of the above R and $R^2$. Furthermore, preferred form of m in the above Formula (2) is also the same as above n.

Examples of the polyalkyleneimine which is a raw material include polyethyleneimine, polypropyleneimine, and polybutyleneimine. Among them, polyethyleneimine is preferable. Among the primary amino group, the secondary amino group, and the tertiary amino group that are present in polyalkyleneimine, a ratio of the total of the primary amino group and the secondary amino group is preferably 30% by mol or more, more preferably 40% by mol or more, and particularly preferably 50% by mol or more. When the ratio of the total of the primary amino group and the secondary amino group is less than 30% by mol, the amount of the hydrophobic group to be introduced is reduced and/or the ratio of the secondary amino group after introducing the hydrophobic group is reduced, yielding a weaker basic property and poor antimicrobial performance. Meanwhile, the ratio of the primary amino group, the secondary amino group, and the tertiary amino group that are present in polyalkyleneimine can be measured by NMR analysis, titration, or the like.

A weight average molecular weight (Mw) of the polyalkyleneimine derivative of the present invention is preferably 400 or higher, more preferably 700 or higher, and even more preferably 800 or higher from the viewpoint of the antimicrobial performance, persistence of the antimicrobial performance and safety. Furthermore, the upper limit of the weight average molecular weight is, although not particularly limited, 100,000 or lower, preferably 70,000 or lower, more preferably 20,000 or lower, even more preferably 5,000 or lower, and particularly preferably 3,000 or lower. The weight average molecular weight is obtained by the GPC method, and specifically, the values that are measured by the method described in Examples are used.

A number average molecular weight of the polyalkyleneimine derivative is preferably 300 or higher, more preferably 500 or higher, and particularly preferably 600 or higher. Furthermore, the number average molecular weight is 100,000 or lower, preferably 70,000 or lower, more preferably 10,000 or lower, even more preferably 5,000 or lower, and particularly preferably 3,000 or lower.

The preparation ratio (GE/PEI) for a reaction of glycidyl ether (GE) with polyalkyleneimine (PEI) is preferably 0.7 or less, more preferably 0.6 or less, even more preferably 0.5 or less, and particularly preferably 0.3 or less. The lower limit of the preparation ratio (GE/PEI) for a reaction of glycidyl ether (GE) with polyalkyleneimine (PEI) is, although not particularly limited, preferably 0.05 or more, and more preferably 0.1 or more. When the ratio is within this range, sufficient antimicrobial performance can be obtained. Furthermore, when the ratio between the polyalkyleneimine and glycidyl ether is 0.3 or less, excellent solubility in water is obtained. Herein, the preparation ratio for a reaction of glycidyl ether with polyalkyleneimine is expressed as follows by using the amine value of the polyalkyleneimine and the epoxy equivalent of the glycidyl ether.

[Mathematical Formula 1]

$$\text{Preparation ratio} = \frac{\text{Amount of glycidyl ether (g)} \times 1000/\text{Epoxy equivalent (g/eq)}}{\text{Amount of polyalkyleneimine (g)} \times \text{Amine value (mol/g)}}$$

The addition reaction is not particularly limited but can be carried out in the presence or absence of a solvent. It is preferably a solvent-free reaction or a reaction in which water or an organic solvent is used as a solvent. More preferably, it is a solvent-free reaction. Furthermore, the reaction can be performed either with stirring or not. However, it is preferable that the reaction is performed with stirring.

As for the solvent which can be used for the addition reaction, one kind or two or more kinds can be suitably selected from the followings and used: water; lower alcohol such as methanol, ethanol, or isopropanol; amides such as dimethyl formamide; ethers such as diethyl ether, tetrahydrofuran, or dioxane; or the like.

Concentration of the raw material at the time of using the above solvent is not particularly limited. However, the total amount of the polyalkyleneimine and glycidyl ether is preferably 10% by weight or more, more preferably 20% by weight or more, and even more preferably 30% by weight or more. If the concentration of the raw material is less than 10% by weight, the reaction time is extended, and therefore undesirable.

As for the above addition reaction, both the polyalkyleneimine and glycidyl ether can be added all at once, or any one of them is prepared at initial stage and the other is added dropwise. However, it is preferably a method in which the polyalkyleneimine is prepared at initial stage and the glycidyl ether is added dropwise.

In the addition reaction, a catalyst is basically not necessary. However, as long as the reaction is not adversely affected by it, the catalyst can be suitably used as required, and a tertiary amine is preferable. Use of an acid as a catalyst is not desirable as there is sometimes a case in which quaternization occurs.

A Reaction temperature for the addition reaction is, although not particularly limited, preferably 30° C. or higher, more preferably 40° C. or higher, and particularly preferably 50° C. or higher. When the reaction temperature is lower than 30° C., the reaction time is extended or unreacted glycidyl ether may increase; therefore, it is undesirable. Furthermore, the reaction temperature is preferably 100° C. or lower, more preferably 90° C. or lower, and even more preferably 80° C. or lower. When the reaction temperature is high, a side reaction like polymerization reaction of glycidyl ether may occur; therefore, it is undesirable. Furthermore, the reaction time for the addition reaction is also not particularly limited, and it can be suitably adjusted depending on reaction temperature, reaction scale, or the like.

For carrying out the above addition reaction, it is preferable that the reaction is carried out under nitrogen atmosphere in order to suppress coloration of a derivative to be obtained. The atmosphere for the addition reaction can be suitably set depending on the purpose of using a derivative to be obtained. Meanwhile, the reaction can be carried out under normal pressure (atmospheric pressure), under pressure, or reduced pressure.

An amount of unreacted glycidyl ether in the polyalkyleneimine derivative introduced with a hydrophobic group of the present invention is preferably 5% by weight or less, more preferably 3% by weight or less, and even more preferably 1% by weight or less. If the amount of unreacted glycidyl ether is more than 5% by weight, an unexpected side reaction may occur when it is blended in a product; therefore, it is undesirable.

The polyalkyleneimine derivative of the present invention is used as an antimicrobial agent. Examples of the use thereof include a use as cleaning agents such as a laundry cleaning agent, a softening agent, a dishwashing agent, and an agent for cleaning hard surfaces; a use as cosmetics such as shampoo, rinse, cosmetic product, and an antiperspirant; and an agent for industrial use such as paint, a wood preservative, a cement admixture, and industrial water (for example, water for paper making step in paper-manufacturing process, cooling water or cleaning water for various industrial uses).

When the antimicrobial agent of the present invention is used after being diluted with a solvent or the like, the addition amount is 20% by weight or less, preferably 10% by weight or less, and more preferably 5% by weight or less. Meanwhile, because a smaller lower limit (that is, higher than 0% by weight) is more preferred for the addition amount, the lower limit is not particularly limited, but when it is present at 0.1% by weight or more, a sufficient effect can be exhibited in general.

As a method for evaluating the antimicrobial performance of the antimicrobial agent of the present invention, there is a method of evaluating bacteriostatic performance and a method of evaluating bactericidal performance. As a method for evaluating bacteriostatic performance, there is a method for evaluating minimum growth inhibitory concentration (MIC). As for the method for evaluating MIC, the measurement can be made based on M26-A according to CLSI (Clinical and Laboratory Standards Institute) of the United States. The MIC value is preferably 300 ppm or less, more preferably 200 ppm or less, even more preferably 100 ppm or less, and particularly preferably 80 ppm or less. If the MIC value is more than 300 ppm, the amount of an antimicrobial agent to be added for exhibiting the bacteriostatic performance becomes high; therefore, it is undesirable.

Furthermore, as a method for evaluating the bactericidal performance, the measurement can be made based on M26-A according to CLSI of the United States or E2315-03 according to American Society for Testing and Materials (ASTM) of the United States. According to the evaluation method described in M26-A, when microbes are kept statistically for 24 hours in a medium added with the microbial agent, the minimum concentration in which viable bacteria count is decreased by 99.9% or more is expressed as minimum bactericidal concentration (MBC). The MBC value is preferably 500 ppm or less, more preferably 300 ppm or less, even more preferably 200 ppm or less, and particularly preferably 100 ppm or less. If the MBC value is more than 500 ppm, the amount of an antimicrobial agent to be added for exhibiting the bactericidal performance becomes high; therefore, it is undesirable. Furthermore, according to the evaluation method using ASTM E2315-03, compared to the number of viable cells of control (no addition of the microbial agent), a value in which a decrease in the number of viable cells in case of adding the microbial agent is expressed in terms of a logarithmic value (log), is described as bactericidal activity value. For example, when the number of viable cells of control is 107 and the number of viable cells in case of adding the antimicrobial agent is $10^2$, the bactericidal activity value is 5. The bactericidal activity value is preferably 1 or more, and particularly preferably 2 or more. When the bactericidal value is less than 1, there is no sufficient bactericidal effect.

According to the present invention, an antimicrobial agent containing a polyalkyleneimine derivative and an alkali modifying agent is also an embodiment of the present invention. Namely, it is preferable that the antimicrobial agent of the present invention further contains an alkali modifying agent. The alkali modifying agent is not particularly limited, and examples thereof include sodium hydroxide, potassium hydroxide, monoethanolamine, diethanolamine, sodium citrate, and sodium carbonate.

The antimicrobial agent of the present invention may be used either as it is or after being diluted with water. According to a preferred embodiment of the present invention, the antimicrobial agent of the present invention is diluted with water, which is provided as a liquid containing the antimicrobial agent of the present invention. A pH of a liquid containing the antimicrobial agent of the present invention is not particularly limited, and at any condition like acidity, neutrality, and alkalinity, good antimicrobial performance can be exhibited. Namely, the antimicrobial agent of the present invention can be used in a pH range of from 2 to 14.

As one embodiment of the present invention, a liquid containing the antimicrobial agent of the present invention may further contain an alkali modifying agent. In that case, the addition amount of an alkali modifying agent is, although it is not particularly limited, an amount such that the pH of a liquid containing the antimicrobial agent of the present invention, which is added with an alkali modifying agent, is 7.1 to 14. In such a range, more efficient working of a damage on a cell wall can be achieved so that higher antimicrobial activity is obtained. A pH of a liquid containing the antimicrobial agent of the present invention and an alkali modifying agent is more preferably 8 to 13, even more preferably 9 to 12.8, and most preferably 10 to 12.5.

According to the present invention, an antimicrobial agent containing a polyalkyleneimine derivative and an anionic surfactant is also a preferred embodiment of the present invention. Namely, it is preferable that the antimicrobial agent of the present invention further contains an anionic surfactant. In that case, examples of the anionic surfactant which may be used is, although not particularly limited, linear alkylbenzene sulfonic acid or a salt thereof (LAS), palm oil fatty acid salt, linear alkylbenzenesulfuric acid salt, polyoxyalkylenealkyl ether sulfuric acid salt (AES), alkyl ether sulfonic acid salt (AS), and fatty acid soap. The anionic surfactant may be either a single member or a two or more members thereof. With regard to the addition amount of the anionic surfactant, addition can be made so as to have an addition amount suitable for functioning as a surfactant. It is preferable to have the addition such that the total amount of the anionic surfactant is preferably 50 ppm or more, and more preferably 100 ppm or more.

The antimicrobial agent of the present invention can be used as a composition as it is combined with a surfactant, a calcium ion remover, a builder for detergent, an antifoaming agent, water soluble salts, a solvent, a preservative, an anti-oxidant, a dye or a pigment, an enzyme, or the like.

Specific examples of the surfactant which may be combined with the antimicrobial agent of the present invention include, in addition to the aforementioned anionic surfactant, a non-ionic surfactant, a cationic surfactant, and an amphoteric surfactant, and one kind or two or more kinds of them may be used. Examples of the non-ionic surfactant include, although not particularly limited, polyoxyalkylenealkyl or alkenyl ether (for example, polyoxyethylenelauryl ether), polyoxyalkylenealkyl phenyl ether, higher fatty acid alkanolamide or an alkylene oxide adduct thereof, sucrose fatty acid ester, alkylglycoside, fatty acid glycerin monoester, and alkylamine oxide. Examples of the cationic surfactant include, although not particularly limited, a quaternary ammonium salt like alkyltrimethylammonium salt (for example, hexadecyltrimethyl ammonium chloride), and examples of the amphoteric surfactant include, although not particularly limited, a carbobetaine type and a sulfobetaine type.

Examples of the calcium ion remover include, although not particularly limited to the followings, citric acid, malic acid, succinic acid, polyacrylic acid, a copolymer of acrylic acid and maleic acid, oxydisuccinic acid, nitrilo triacetic acid, iminodisuccinic acid, disuccinic acid, tartaric acid, monosuccinic acid, ethylene diamine tetraacetic acid, pyrophosphoric acid, and a mixture thereof.

Examples of a builder for detergent include a water soluble polymer such as acrylic acid/maleic acid copolymer salt, polyethylene glycol, sodium tripolyphosphate, sodium pyrophosphate, sodium silicate, sodium carbonate, sodium sulfate, sodium nitrilotriacetate, sodium ethylene diamine tetraacetate, potassium ethylene diamine tetraacetate, carboxy derivatives of polysaccharides, or fumaric acid (co)polymer salt.

Examples of the anti-foaming agent include a silicone anti-foaming compound, silicone emulsion, 2-alkyl and alkanol anti-foaming compound, mineral oil emulsion, hydrocarbon oil emulsion, polyalkylene emulsion, and a mixture thereof.

Examples of the water soluble salts include inorganic or organic water soluble salts. Examples of the inorganic or organic water soluble salts include, in addition to sodium chloride, potassium chloride, calcium chloride, magnesium chloride or the like, an alkali metal salt or an alkali earth metal salt of sulfuric acid or nitric acid, and an alkali metal salt of an organic acid such as p-toluene sulfonic acid, glycolic acid, and lactic acid. Preferred is calcium chloride or sodium chloride.

Examples of the solvents include an alcohol solvent such as methanol, ethanol, or n-propanol, a glycol solvent such as ethylene glycol, diethylene glycol, polyethylene glycol, or propylene glycol, an aliphatic alcohol such as myristyl alcohol, cetyl alcohol, or 2-hexadecaonol, a ketone solvent such as acetone, methyl ethyl ketone, methylisobutyl ketone, or propyplene carbonate, an ether solvent such as dioxane, tetrahydrofuran, or ethyl ether, an ester solvent such as ethyl acetate, butyl acetate, isobutyl acetate, 3-methyl-3-methoxybutyl acetate, γ-butyrolactone, dimethyl adipate, dimethyl glutarate, or dimethyl succiniate, and a polar solvent such as dimethyl formamide, dimethyl acetamide, dimethyl sulfoxide, acetonitrile, or N-methyl pyrrolidone.

A preservative may be blended to enhance the preservation property of the antimicrobial agent of the present invention during long term storage, and examples thereof include an isothiazolone-based organic sulfur compound, a benzisothiazolone-based organic sulfur compound, benzoic acids, an alcohol-based 2-bromo-2-nitropropane-1,3-diol, and an iodine-based compound.

The antimicrobial agent of the present invention may contain other antimicrobial compound, and examples thereof include an organic antimicrobial agent such as an iodine-based compound, a triazole-based compound, a sulfamide-based compound, a bis quaternary ammonium salt-based compound, a quaternary ammonium salt-based compound, a phthalonitrile-based compound, a dithiol-based compound, a thiophene-based compound, a thiocarbamate-based compound, a nitrile-based compound, a phthalimide-based compound, a haloalkylthio-based compound, a pyridine-based compound, a pyrithione-based compound, a benzothiazole-based compound, a triazine-based compound, a guanidine-based compound, a urea-based compound, an imidazole-based compound, an isothiazobenzothiazole-based compound, a trialline-based compound, a nitroalcohol-based compound, or a phenylurea-based compound, and an inorganic antimicrobial agent such as silver, zinc, or copper.

The anti-oxidant may be blended to improve the color stability of the antimicrobial composition, and examples of the anti-oxidant include ascorbic acid, ascorbic acid palmitate, propyl gallate, BHT (dibutylhydroxy toluene), BHA (butylated hydroxyanisole), a mixture of propyl gallate and citric acid, hydroquinone, tertiary butylhydroquinone, trehalose of disaccharides, natural tocopherol-based compound, long chain ester (carbon atom number of 8 to 22) of gallic acid like dodecyl gallate, citric acid, isopropyl citrate, 4,5-dihydroxy-m-benzene sulfonate or a sodium salt thereof, dimethoxyphenol, catechol, methoxyphenol, carotenoid, furans, and amino acids.

The dye and pigment may be blended for the purpose of improving the appearance of a composition containing the antimicrobial agent. As for the dye and pigment, dyes and pigments that are conventionally used for an antimicrobial agent can be used. Although they are not particularly limited, preferred examples thereof include at least one water soluble dye with red color, blue color, yellow color, or purple color which is selected from an acidic dye, a direct dye, a basic dyes, a reactive dye, and a mordant-acidic mordant dye.

Examples of the enzyme include cellulase, amylase, protease, lipase, and keratinase.

The antimicrobial agent of the present invention may be suitably combined with, other than those above, a reducing agent, an emulsifying agent (for example, polystyrene emulsion), an opacifier, a shrinkage inhibitor, a laundry wrinkle inhibitor, a shape maintaining agent, a drape property maintaining agent, an ironing property enhancing agent, a bleach (for example, sodium persulfate, sodium perborate, or the like), a bleach activator (for example, nonanoyl oxybenzene sulfonate, tetraacetyl ethylene diamine, or the like), a brightening agent, a whitening agent, a cloth softening clay, an anti-static agent, a dye transfer inhibitor (for example, polyvinyl pyrrolidone), a polymer dispersing agent, a dirt releasing agent, a scum dispersing agent, a fluorescent brightening agent, a dye fixing agent, a discoloration inhibitor, a stain removing agent, silk protein powder to provide texture function of silk like water absorbing and releasing property, a surface modifying product, an emulsifying dispersion, a contamination inhibitor, an ultraviolet absorbing agent, a fragrance, and a precipitation aid.

The antimicrobial agent of the present invention and a composition containing the antimicrobial agent may be also used, other than the applicational use described above, in combination with a personal care product, a product for caring household goods, a skin care product, or the like, and it may be also used for paint, ink, resin emulsion, metal processing oil, or other industrial applications.

Therefore, according to one embodiment of the present invention, a personal care product, a product for caring household goods, or a skin care product containing the antimicrobial agent of the present invention is provided. As the antimicrobial agent of the present invention is contained in a personal care product, a product for caring household goods, or a skin care product, not only the antimicrobial effect but also the adsorption persistence of the antimicrobial agent for a subject of the above products, for example, clothes, hair, skin, or the like, is improved. Namely, the antimicrobial agent may have a persistent antimicrobial effect. Although the mechanism for having improved adsorption persistence of the antimicrobial agent of the present invention remains unclear, it is presumed as follows.

The antimicrobial agent of the present invention contains the polyalkyleneimine derivative described above, and the polyalkyleneimine derivative of the present invention has a structure in which a hydrophobic group is introduced to the nitrogen atom of the polyalkyleneimine and a hydroxyl group and an ether group are present between the nitrogen atom of the polyalkyleneimine and the hydrophobic group. When an ether group is present between an amino group which has an adsorption property for fibers, hair, or skin and a hydrophobic group which has a water-resistant property, the hydrophobic group can freely move via the oxygen atom so that the effect of the amino group and hydrophobic group can be more efficiently exhibited. It is thought that, as the polyalkyleneimine derivative has the above structure, a personal care product, a product for caring household goods, or a skin care product can easily adsorb on a subject for use (for example, clothes, hair, and skin), and washout by water or the like from the subject can be suppressed (that is, remaining property is improved). Meanwhile, the above mechanism is just an assumption, and the present invention is not limited to the above mechanism.

In the present specification, the "adsorption persistence" means a remaining property of the polyalkyleneimine derivative according to the present invention. Furthermore, the personal care product indicates a product which is used for the purpose of cleaning, decorating, or satisfying preferences of a human body. The product for caring household goods is a product which is used for cleaning or sterilizing a product used in a house (for example, fiber product, synthetic resin processed product, electric and mechanical instrument, and miscellaneous industrial product). The skin care product is a product which is used for maintaining well or protecting a skin state or the like.

Preferred examples of the personal care product which contains the antimicrobial agent of the present invention include, although not particularly limited to the followings, hand soap, a disinfecting agent for hands, a body cleanser, an oral cavity washer, cream toothpaste, shower gel, a hair washing composition such as shampoo or conditioner, a hair-grooming agent, an anti-perspirant, body lotion, a deodorant composition such as deodorant, a nasal spray, a foot care product, a vagina care product, a vagina cleaning agent, a pet animal care product, and a combination thereof. Examples of other personal care products include a wipe product, in particular, a wipe product suitable for wiping or drying a face or a hand, for example, a product in the form of tissue, towel, or the like. In those cases, the antimicrobial agent of the present invention is preferably bound to the above wipe product or impregnated therein. Furthermore, other examples of the personal care product include a product form including a feminine napkin, a product form like diaper, and use for skin with inflammation, injured skin, or skin with acne, or an emergency disinfecting agent for use after surgery, or the like.

In case of a hair washing composition as a personal care product containing the antimicrobial agent of the present invention, a content of the antimicrobial agent in the composition is not particularly limited and it can be suitably adjusted. A lower limit of the content is, from the viewpoint of the antimicrobial property and adsorption persistence, preferably 0.001% or more, and more preferably 0.01% or more relative to the total amount of the hair washing composition (100% by weight). An upper limit of the content is, from the viewpoint of suppressing a decrease in cleaning ability, preferably 5% or less, and more preferably 2% or less. Furthermore, a lower limit of the hair remaining ratio of the hair washing composition is, from the viewpoint of extending the antimicrobial effect, preferably 10% or more, and more preferably 12% or more. An upper limit of the hair remaining ratio of the hair washing composition is, although not particularly limited, 30% or less, for example. Meanwhile, as for the hair remaining ratio, values measured by the method described in Examples are used.

In case of a deodorant composition as a personal care product containing the antimicrobial agent of the present invention, a content of the antimicrobial agent in the composition is not particularly limited and it can be suitably adjusted. A lower limit of the content is, from the viewpoint of the antimicrobial property and adsorption persistence, preferably 0.001% or more, and more preferably 0.01% or more relative to the total amount of the deodorant composition (100% by weight). An upper limit of the content is, from the viewpoint of suppressing the skin-irritating property, preferably 5% or less, and more preferably 3% or less. Furthermore, a lower limit of the skin-remaining ratio the deodorant composition is, from the viewpoint of extending the antimicrobial effect, preferably 4% or more, and more preferably 5% or more. An upper limit of the skin-remaining ratio of the deodorant composition is, although not particularly limited, 10% or less, for example. Meanwhile, as for the skin-remaining ratio, values measured by the method described in Examples are used. Furthermore, according to the deodorant composition containing the antimicrobial agent of the present invention, components as a cause of having malodor like aldehyde can be adsorbed by the antimicrobial agent. As such, the deodorant composition of the present invention not only can suppress an occurrence of malodor by microbes but also can have a deodorant effect in case of having malodor.

Examples of the product for caring household goods containing the antimicrobial agent of the present invention include, although not limited to the followings, a detergent for clothing materials, a softening agent, a cleaner for hard surfaces, a deodorant, a cloth care composition, a cloth cleaning composition, a detergent for hand-dishwashing, a detergent for automated dishwasher, a floor care composition, a kitchen cleaner, a kitchen disinfectant, a bathroom cleaner, a bathroom disinfectant, and a combination thereof. Examples of other product for caring household goods include a wiping product, a towel, or the like which is useful for cleaning of household goods or caring of household goods. Furthermore, the product for caring household goods may contain a specific auxiliary component. Examples of the auxiliary component include, although not limited to the followings, an enzyme with cleaning property, a builder, a bleach, a bleach activating agent, a transition metal bleach catalyst, an oxygen carrier, an enzyme precursor, a dirt releasing agent, a clay remover, a re-adsorption inhibitor, a polymer dispersant, a brightening agent, a polymer dye transfer inhibitor, a chelating agent, an anti-foaming agent, an alkoxylated polycarboxylates, a cloth softener, a fragrance, a carrier, a hydro tropic material, a processing aid, a dye, a pigment, a solvent for preparing liquid, a solid filler, a surfactant with cleaning property, and a combination thereof.

In case of a cleaning composition for clothing materials as a product for caring household goods containing the antimicrobial agent of the present invention, a content of the antimicrobial agent in the composition is not particularly limited and it can be suitably adjusted. A lower limit of the content is, from the viewpoint of the antimicrobial property and adsorption persistence, preferably 0.1% or more, and more preferably 0.5% or more. An upper limit of the content is, from the viewpoint of suppressing a decrease in the cleaning ability, preferably 10% or less, and more preferably 5% or less.

When a cleaning composition for clothing materials is added to a washing liquid, a content of the antimicrobial agent is not particularly limited and it can be suitably adjusted. A lower limit of the content is, from the viewpoint of the antimicrobial property and adsorption persistence, preferably 1 ppm or more, and more preferably 5 ppm or more. An upper limit of the content is, from the viewpoint of suppressing a decrease in the cleaning ability, preferably 300 ppm or less, and more preferably 100 ppm or less.

A weight ratio between the antimicrobial agent and anionic surfactant in the composition for clothing materials (anionic surfactant/antimicrobial agent) is, from the viewpoint of suppressing a decrease in the cleaning ability, preferably 1 or higher, and more preferably 2 or higher. An upper limit of the content is, from the viewpoint of the antimicrobial property and adsorption persistence, preferably 50 or less, and more preferably 30 or less.

Preferred examples of the skin care product which contains the antimicrobial agent of the present invention include, although not particularly limited to the followings, a skin lotion, a milky lotion, a moistening agent, an ultraviolet blocking agent, and an anti-aging agent. Furthermore, the skin care product may also contain a specific auxiliary component, and examples of the auxiliary component include an anti-bacterial and anti-fungi active material, a surfactant, a peeling active material, an anti-acne active material, an anti-wrinkle active material, an anti-skin shrinking active material, an anti-oxidant, a radical scavenger, a chelating agent, flavonoids, an anti-inflammatory agent, an anti-cellulite agent, local anesthetics, a suntan active material, an ultraviolet blocking active material, a conditions agent, a thickening agent, a stickiness removing agent, a flavoring agent, a skin sensitizing agent, an anti-perspirant, and a mixture thereof.

The antimicrobial agent of the present invention can be also used for a paint, and examples of the paint include oil-based paint, ethanol-based paint, NAD paint, electrodeposition paint, powder paint, cellulose paint, synthetic resin paint, aqueous paint, poison ivy-based paint, and rubber paint. Preferably, application is made for synthetic resin paint and aqueous paint. Furthermore, the above paints are also used for architectural application, paper making application, automobile application, ship application, and heavy duty anti-corrosion application, or the like.

The antimicrobial agent of the present invention can be also used for an ink, and the ink may be oil-based ink, aqueous ink, or the like, and it is not particularly limited. Examples thereof include ink for handwriting, ink for printing, ink for copying, ink for marking, and special ink (for example, permanent ink and invisible ink). Preferably, it is applied for the aqueous ink.

The antimicrobial agent of the present invention can be also used for an aqueous emulsion. The aqueous emulsion is not particularly limited and examples thereof include acrylic resin emulsion, urethane resin emulsion, vinyl acetate resin emulsion, acrylic-styrene resin emulsion, and ethylene-vinyl acetate resin emulsion. Preferably, it is applied for acrylic resin emulsion and vinyl acetate resin emulsion.

The antimicrobial agent of the present invention can be also used for a metal processing oil. The metal processing oil is oil used for metal processing of a metal material, and it is not particularly limited including water-insoluble metal processing oil and water-soluble metal processing oil. Examples thereof include cutting oil, grinding oil, and working oil. Preferably, it is applied for water-soluble metal processing oil.

The antimicrobial agent of the present invention can be also used for other industrial applications, and for example, it may be used for various kinds of industrial water (for example, water used in paper-making pulp plant and cooling water used for cooling water circulation step), adhesives (for example, aqueous or hydrophilic adhesives and oily adhesives), film materials (for example, coating paper, polyvinyl alcohol film, and polyvinyl chloride film), plastic products (for example, molded articles such as housing or casing), cement admixture, and building materials (for example, gypsum board, plaster, ceiling material, fiber wall, various joint fillers, sealant, and wall paper).

EXAMPLES

Hereinbelow, the present invention is explained more specifically in view of Examples and Comparative Examples, but it is evident that the present invention is not limited to them.

Antimicrobial performance of the polyalkyleneimine derivative was measured according to the following method.

[Minimum Growth Inhibitory Concentration (MIC)]

An aqueous solution containing the antimicrobial agent was serially diluted by two fold with a Mueller-Hinton medium to prepare dilution series of a medium containing the antimicrobial agent. After that, the medium containing the antimicrobial agent at each concentration was added, in an amount of 50 µl each, to a 96 well polystyrene plate. Next, colonies of *Escherichia coli* (NBRC-3972) and/or *Staphylococcus aureus* (NBRC-12732) which have been grown for 18 hours in a Mueller-Hinton agar medium were suspended in a Butterfield's buffer solution to prepare a liquid containing microbial cells of $10 \times 10^8$ cells/mL or so. The prepared liquid containing microbial cells was diluted to $10 \times 10^6$ cells/mL or so in a Mueller-Hinton medium, and added in an amount of 50 µl to each of the dilution series prepared in the above. After keeping them for 20 hours at 35° C., the minimum concentration of the antimicrobial agent (ppm) in a medium in which the bacterial cells did not grow was determined as minimum growth inhibitory concentration (MIC). Presence or absence of the growth of the bacterial cells was determined with a naked eye by following an increase in turbidity.

[Bactericidal Activity Value]

The in vitro bactericidal test was carried out on the basis of the method described in E-2315-03 of ASTM (American Society for Testing and Materials) standards. First, *Escherichia coli* or *Staphylococcus aureus* were cultured for 18 hours at 35° C. using a Mueller-Hinton medium agar medium (manufactured by Wako Pure Chemical Industries, Ltd.), and the emerged colonies were scraped off using a Butterfield's buffer solution (0.0425 g/L potassium dihydrogen phosphate buffer solution, adjusted to pH of 7.2), and adjusted to $10 \times 10$ CFU/L or so. An aqueous solution added with 50 ppm of the antimicrobial agent was prepared to have various pHs, and the liquid of bacterial cells which has been prepared above was added thereto in an amount of 1% by weight followed by stirring and keeping for 60 seconds. After that, the activity of the antimicrobial agent was terminated by adding a neutralizing agent. After dilution, the test solutions were spread on a Mueller-Hinton agar medium and the number of viable cells was counted after 20 hours. As for the neutralizing agent to terminate the activity of the antimicrobial agent, 0.7 g/L of lecithin and 5 g/L aqueous solution of polysorbate 80, which has been confirmed with the neutralization of the antimicrobial effect of the antimicrobial agent of the present test based on the method prescribed in ASTM E1054-08, were used. As for the bactericidal activity value, the value obtained by subtracting a base 10 logarithmic value after the treatment from a base 10 logarithmic value of the initial viable cell count was used.

The bacterial cell lines used herein are described below. *Escherichia coli*; *Escherichia coli*, NBRC-3972 *Staphylococcus aureus*; *Staphylococcus aureus*, NBRC-12732.

[Anti-Fungal Test]

*Cladosporium cladosporioides* (NBRC 6348) were inoculated to a potato dextrose slant agar medium (PDA slant medium manufactured by Wako Pure Chemical Industries, Ltd.), and then subjected to static culture for 4 days at 25° C. 10 mL of a 50 ppm aqueous solution of sodium dioctyl sulfosuccinate was added thereto to suspend spores, and then filtration was performed by using a gauze. After measuring the number of the spores in the filtrate, centrifuge was performed followed by washing with pure water to prepare a spore solution of $10^6$ CFU/mL. The spore solution prepared as above was applied in an amount of 100 μl to a potato dextrose agar medium in which the polymer obtained from Preparation Example 1 is contained at 200 ppm. It was then subjected to static culture at 25° C. Observation was made to see the presence or absence of fungi growth, and the anti-fungi property was evaluated according to the following criteria.

[Chemical Formula 5]

○: Fungi growth was not observed at all.

Δ: Slight fungi growth was observed.

X: Fungi growth was observed from the entire plate surface.

[Minimum Bactericidal Concentration (MBC)]

An aqueous solution containing the antimicrobial agent was serially diluted by two fold with a Mueller-Hinton medium to prepare dilution series of a medium containing the antimicrobial agent. After that, the medium containing the antimicrobial agent at each concentration was added, in an amount of 50 μl each, to a 96 well polystyrene plate. Next, colonies of *Escherichia coli* (NBRC-3972) or *Staphylococcus aureus* (NBRC-12732) which have been grown for 18 to 24 hours in a Mueller-Hinton agar medium were suspended in a Mueller-Hinton medium incubated at 35° C., shaken for 2 to 6 hours at 35° C., and cultured until the turbidity can be confirmed with a naked eye. The prepared culture liquid was diluted a Mueller-Hinton medium to $10 \times 10^8$ cells/mL or so, and again diluted to 100 times with a Butterfield's buffer solution. The bacterial cell concentration of the obtained liquid of bacterial cells was determined by a plate dilution method, and subsequently, the liquid of bacterial cells was added in an amount of 50 μl to each of the dilution series of the antimicrobial agent which has been prepared above and kept for 24 hours at 35° C. At that time, the procedures were performed simultaneously for both of the cells with keeping for 24 hours at 35° C. (pH 7) and the cells with keeping for 24 hours at 35° C. after pH is adjusted to 10 by adding an aqueous solution of sodium hydroxide (pH 10). From those not showing any growth in each well, 10 μl was taken and diluted to 10 times with a Butterfield's buffer solution, plated for two sets, and viable cell count was measured. Accordingly, the viable cell count in the initial liquid of microbial cells and the viable cell count after treatment for 24 hours in the antimicrobial agent were measured. Then, the minimum addition concentration (ppm) of the antimicrobial agent by which the cell count was reduced by 99.9% or more after the treatment compared to the initial viable cell count was determined as minimum bactericidal concentration (MBC).

[Conversion Rate of Glycidyl Ether]

A conversion rate of glycidyl ether was calculated by quantification of an amount of glycidyl ether remaining in a reaction solution using gas chromatography equipped with FID (manufactured by Shimadzu Corporation, GC-2010) based on internal standard method.

[Introduction Amount of Hydrophobic Group Per Nitrogen Atom]

An introduction amount (% by mol) of a hydrophobic group per nitrogen atom of polyalkyleneimine derivative is calculated based on the following formula.

[Mathematical Formula 2]

$$\text{Introduction amount of hydrophobic group (\% by mol)} = \frac{\text{Amount of } GE \text{ (g)} \times 1000 \times \text{Conversion rate of } GE \times 100/\text{Epoxy equivalents (g/eq)}}{\text{Amount of polyoxyethyleneimine(g)} \times \text{Amine number (mmol/g)}}$$

GE: Glycidyl ether

[Method for Measuring Weight Average Molecular Weight and Number Average Molecular Weight]

Measurement of weight average molecular weight and number average molecular weight based on gel permeation chromatography (GPC) was carried out at the following conditions by using HLC-8320 GPC EcoSEC (manufactured by TOSOH CORPORATION).

Column: SHODEX OHpak SB-802.5HQ, SB-803HQ

Column temperature: 40° C.

Eluent: aqueous solution of 0.5 M acetic acid+0.2 M sodium acetate/acetonitrile=50/50 (volume ratio)

Detector: RI

Calibration curve: standard polyethylene glycol (manufactured by Agilent Technologies).

Preparation Example 1

The polymers 1 to 15 shown in Table 1 were synthesized according to the following order. Meanwhile, the following raw materials were used as a raw material.

Polyethyleneimine

EPOMIN (registered trade mark) SP-003 (the polymer 2; number average molecular weight: 300 [catalogue value], weight average molecular weight: 530), SP-006 (the polymer 1, 4 to 11, 13 to 15; number average molecular weight: 600 [catalogue value], weight average molecular weight: 760), SP-018 (the polymer 3, 12; number average molecular weight: 1,800 [catalogue value], weight average molecular weight: 1,310) (manufactured by Nippon Shokubai Co., Ltd.)

Glycidyl Ether

2-Ethylhexyl glycidyl ether (Denacol (registered trade mark) EX-121; manufactured by Nagase ChemteX Corporation)

Lauryl glycidyl ether (Denacol (registered trade mark) EX-192; manufactured by Nagase ChemteX Corporation)

Lauryl (EO)15 glycidyl ether (Denacol (registered trade mark) EX-171; manufactured by Nagase ChemteX Corporation)

Butyl glycidyl ether (manufactured by Tokyo Chemical Industry Co., Ltd.).

To a 4-necked 500 mL flask equipped with a thermometer, a reflux condenser, and a stirring device, polyethyleneimine (PEI) of the member and amount described in the following Table 1 was prepared, and under stirring, glycidyl ether (GE) of the member and amount described in the following Table 1 was added thereto. This polymer mixture was heated to a temperature of 55° C. and reacted for 8 hours to obtain a polymer. By gas chromatography, the unreacted glycidyl ether was analyzed and the conversion rate of the glycidyl ether was calculated and described as "GE conversion rate (%)" in the following Table 1. Furthermore, the introduction amount of a hydrophobic group per nitrogen atom of the polyethyleneimine was calculated and described as "Introduction amount of hydrophobic group (% by mol)" in the following Table 1.

Preparation Example 3

To an automated synthesizer equipped with rotating stirring device for high viscosity (PPS-2511, manufactured by TOKYO RIKAKIKAI CO., LTD.), a test tube with volume of 30 ml was installed and 10.0 g of polyethyleneimine (EPOMIN SP-003, weight average molecular weight: 530) and 4.66 g of 1-bromodecane were prepared. Under stirring, the temperature was increased to 55° C. and the reaction was allowed to occur for 8 hours. As a result of analysis by gas chromatography, unreacted 1-bromodecane was not detected. The produced salt was separated by filtration and the polymer 17 was obtained. The introduction ratio of a hydrophobic group was 10% by mol and the weight average molecular weight of the polymer 17 was 680. 1% by weight

TABLE 1

| | Polyethyleneimine (PEI) | | | | Glycidyl ether (GE) | | Preparation ratio GE/PEI | GE conversion rate (%) | PEI (g) | GE (g) | Weight average molecular weight (Mw) | Introduction amount of hydrophobic group (% by mol) |
|---|---|---|---|---|---|---|---|---|---|---|---|---|
| | Catalogue value | GPC | | | | | | | | | | |
| | Number average molecular weight (Mn) | Number average molecular weight (Mn) | Weight average molecular weight (Mw) | Amine number (mmol/g) | Member of hydrophobic group | Epoxy equivalents (g/eq) | | | | | | |
| Polymer 1 | 600 | 730 | 760 | 20 | 2-Ethylhexyl | 187 | 0.13 | >99.9 | 491.2 | 238.8 | 990 | 13.0 |
| Polymer 2 | 300 | 500 | 530 | 21 | 2-Ethylhexyl | 187 | 0.13 | >99.9 | 483.3 | 246.7 | 750 | 13.0 |
| Polymer 3 | 1800 | 1240 | 1310 | 19 | 2-Ethylhexyl | 187 | 0.13 | >99.9 | 499.4 | 230.6 | 2150 | 13.0 |
| Polymer 4 | 600 | 730 | 760 | 20 | 2-Ethylhexyl | 187 | 0.05 | >99.9 | 615.0 | 115.0 | 860 | 5.0 |
| Polymer 5 | 600 | 730 | 760 | 20 | 2-Ethylhexyl | 187 | 0.3 | >99.9 | 344.0 | 386.0 | 1290 | 30.0 |
| Polymer 6 | 600 | 730 | 760 | 20 | 2-Ethylhexyl | 187 | 0.5 | >99.9 | 254.4 | 475.6 | 1500 | 50.0 |
| Polymer 7 | 600 | 730 | 760 | 20 | 2-Ethylhexyl | 187 | 0.7 | >99.9 | 201.8 | 528.2 | 1690 | 69.9 |
| Polymer 8 | 600 | 730 | 760 | 20 | Lauryl | 281 | 0.13 | >99.9 | 421.8 | 308.2 | 2090 | 13.0 |
| Polymer 9 | 600 | 730 | 760 | 20 | Lauryl (EO) 15 | 971 | 0.13 | >99.9 | 207.1 | 522.9 | 10650 | 13.0 |
| Polymer 10 | 600 | 730 | 760 | 20 | 2-Ethylhexyl | 187 | 0.1 | >99.9 | 531.3 | 198.7 | 950 | 10.0 |
| Polymer 11 | 600 | 730 | 760 | 20 | 2-Ethylhexyl | 187 | 0.2 | >99.9 | 417.6 | 312.4 | 1110 | 20.0 |
| Polymer 12 | 1800 | 1240 | 1310 | 19 | 2-Ethylhexyl | 187 | 0.2 | >99.9 | 426.8 | 303.2 | 2250 | 20.0 |
| Polymer 13 | 600 | 730 | 760 | 20 | Lauryl | 281 | 0.1 | >99.9 | 467.3 | 262.7 | 1830 | 10.0 |
| Polymer 14 | 600 | 730 | 760 | 20 | Lauryl | 281 | 0.15 | >99.9 | 396.1 | 333.9 | 2200 | 15.0 |
| Polymer 15 | 600 | 730 | 760 | 20 | Butyl | 130 | 0.13 | >99.9 | 545.6 | 184.4 | 915 | 13.0 |

Preparation Example 2

To a 4-necked 200 mL flask equipped with a thermometer, a reflux condenser, and a stirring device, 17.3 g of polyethyleneimine (EPOMIN SP-006, weight average molecular weight: 760) and 69.2 g of tetrahydrofuran (THF) were prepared and the temperature was increased to 55° C. Under stirring, 7.2 g of hexyl bromide and 20.0 g of THF were added dropwise thereto over 1 hour. After the dropwise addition, the reaction was allowed to occur for 8 hours. As a result of analysis by gas chromatography, unreacted hexyl bromide was not detected. The produced salt was separated by filtration and, by removing the THF which has been added as a solvent using an evaporator, the polymer 16 was obtained. The introduction amount of a hydrophobic group was 12.7% and the weight average molecular weight of the polymer 16 was 860. As a result of analysis by gas chromatography, THF as a solvent was not detected.

aqueous solution of the polymer 17 of which pH has been adjusted to 6 by using acetic acid was then prepared.

Preparation Example 4

To an automated synthesizer equipped with rotating stirring device for high viscosity (PPS-2511, manufactured by TOKYO RIKAKIKAI CO., LTD.), a test tube with volume of 30 ml was installed and 10.0 g of polyethyleneimine (EPOMIN SP-006, weight average molecular weight: 760) and 4.81 g of 1,2-epoxyhexadecane were prepared. Under stirring, the temperature was increased to 55° C. and the reaction was allowed to occur for 3 hours. The reaction was further allowed to occur at 85° C. for 8 hours to obtain the polymer 18. As a result of analysis by gas chromatography, unreacted 1,2-epoxyhexadecane was not detected. The introduction ratio of a hydrophobic group was 10% by mol and the weight average molecular weight of the polymer 18 was 900. 1% By weight aqueous solution of the polymer 18 of which pH has been adjusted to 2 by using hydrochloric acid was then prepared.

Preparation Example 5

To an automated synthesizer (PPS-2511, manufactured by TOKYO RIKAKIKAI CO., LTD.), a test tube with volume of 30 ml was installed and 2.90 g of diethylenetriamine (manufactured by Tokyo Chemical Industry Co., Ltd.) was prepared. Under stirring, 7.00 g of 2-ethylhexy glycidyl ether was added dropwise thereto, and the temperature was increased to 55° C. under stirring and the reaction was allowed to occur for 3 hours. The reaction was further allowed to occur at 85° C. for 8 hours to obtain the polymer 19. As a result of analysis by gas chromatography, unreacted 2-ethylhexyl glycidyl ether was not detected. The introduction ratio of a hydrophobic group was 45% by mol. The obtained polymer 19 was dissolved in water, but white turbidity was shown and the polymer was insoluble in water. As such, depending on the evaluation method, 1% by weight aqueous solution of the polymer 19 of which pH has been adjusted to 6 by using hydrochloric acid was prepared.

Examples 1 to 14 and Comparative Examples 1 and 2

Minimum growth inhibitory concentration (MIC) was obtained for the polymers 1 to 15, which have been obtained in Preparation Example 1, and polyethyleneimine (EPOMIN SP-006; number average molecular weight (Mn): 600 [catalogue value]) not introduced with any hydrophobic group. The results are shown in Table 2.

TABLE 2

| | | MIC (ppm) | |
|---|---|---|---|
| | Antimicrobial agent | Escherichia coli | Staphylococcus aureus |
| Example 1 | Polymer 1 | 20 | 8 |
| Example 2 | Polymer 2 | 125 | 31 |
| Example 3 | Polymer 3 | 63 | 8 |
| Example 4 | Polymer 4 | 125 | 16 |
| Example 5 | Polymer 5 | 13 | 6 |
| Example 6 | Polymer 6 | 13 | 13 |
| Example 7 | Polymer 7 | 125 | 125 |
| Example 8 | Polymer 8 | 64 | 16 |
| Example 9 | Polymer 9 | 125 | 63 |
| Example 10 | Polymer 10 | 31 | 8 |
| Example 11 | Polymer 11 | 16 | 8 |
| Example 12 | Polymer 12 | 31 | 16 |
| Example 13 | Polymer 13 | 63 | 16 |
| Example 14 | Polymer 14 | 63 | 16 |
| Comparative Example 1 | Polyethyleneimine (Mn = 600) | 625 | 40 |
| Comparative Example 2 | Polymer 15 | 500 | 39 |

Examples 15 to 20

Minimum bactericidal concentration (MBC) was obtained for the polymers 5 and 10 to 14, which have been obtained in Preparation Example 1. The results are shown in Table 3.

TABLE 3

| | | MBC (ppm) | | |
|---|---|---|---|---|
| | | pH 7 | | pH 10 |
| | Antimicrobial agent | Escherichia coli | Staphylococcus aureus | Staphylococcus aureus |
| Example 15 | Polymer 5 | 16 | 8 | 3 |
| Example 16 | Polymer 10 | 63 | 16 | 3 |
| Example 17 | Polymer 11 | 31 | 8 | 6 |
| Example 18 | Polymer 12 | 63 | 16 | 6 |
| Example 19 | Polymer 13 | 63 | 16 | 2 |
| Example 20 | Polymer 14 | 63 | 16 | 2 |

Examples 21 to 27 and Comparative Example 3

Based on ASTM E-2315-03, a bactericidal property test was carried out with contact time of 1 minute for an aqueous solution in which the polymers 1, 5 or 10 to 14 which have been obtained in Preparation Example 1 or the polymer 16 which has been obtained in Preparation Example 2 was added in an amount of 50 ppm. The results are shown in Table 4. From Table 4, it was found that, even with contact for a short period of time, the polymers 1, 5, and 10 to 14 exhibit a high bactericidal effect for Escherichia coli and Staphylococcus aureus. Meanwhile, when the polymer 1 and the polymer 16, both having the same introduction ratio of hydrophobic group, are compared to each other, it was shown that the polymer 16 has a high bactericidal effect for Staphylococcus aureus but a low bactericidal effect for Escherichia coli.

TABLE 4

| | | Bactericidal activity value | |
|---|---|---|---|
| | Antimicrobial agent | Escherichia coli | Staphylococcus aureus |
| Example 21 | Polymer 1 | 5.8 | 4.6 |
| Example 22 | Polymer 5 | 5.1 | >5.1 |
| Example 23 | Polymer 10 | 1.1 | 5.1 |
| Example 24 | Polymer 11 | 5.1 | >5.1 |
| Example 25 | Polymer 12 | 5.1 | 5.1 |
| Example 26 | Polymer 13 | 1.6 | 3.7 |
| Example 27 | Polymer 14 | 1.1 | 3.5 |
| Comparative Example 3 | Polymer 16 | 2.7 | 5.3 |

Examples 28 to 35 and Comparative Example 4

By using the polymers 1, 5, 8, and 10 to 14 which have been obtained in Preparation Example 1, MIC was measured in the presence of an anionic surfactant. As for the anionic surfactant, linear alkylbenzene sulfate was used at 80 ppm and polyoxyalkylenealkyl ether sulfate was used at 80 ppm. The results are shown in Table 5. From Table 5, it is found that the bacteriostatic effect can be exhibited with a smaller addition amount compared to benzalkonium chloride, which is a conventionally used as antimicrobial agent.

TABLE 5

| | Antimicrobial agent | MIC (ppm) |
|---|---|---|
| Example 28 | Polymer 1 | 125 |
| Example 29 | Polymer 5 | 250 |

TABLE 5-continued

| | Antimicrobial agent | MIC (ppm) |
|---|---|---|
| Example 30 | Polymer 8 | 250 |
| Example 31 | Polymer 10 | 125 |
| Example 32 | Polymer 11 | 250 |
| Example 33 | Polymer 12 | 250 |
| Example 34 | Polymer 13 | 250 |
| Example 35 | Polymer 14 | 250 |
| Comparative Example 4 | Benzalkonium chloride | 625 |

Examples 36 to 41

By using the polymers 5 and 10 to 14 which have been obtained in Preparation Example 1, MBC was measured in the presence of an anionic surfactant. As for the anionic surfactant, linear alkylbenzene sulfate was used at 80 ppm and polyoxyalkylenealkyl ether sulfate was used at 80 ppm. The results are shown in Table 6. From Table 6, it is found that the polymers of the present invention can exhibit the bactericidal effect even with a small addition amount.

TABLE 6

| | Antimicrobial agent | MBC (ppm) |
|---|---|---|
| Example 36 | Polymer 5 | 250 |
| Example 37 | Polymer 10 | 125 |
| Example 38 | Polymer 11 | 250 |
| Example 39 | Polymer 12 | 500 |
| Example 40 | Polymer 13 | 250 |
| Example 41 | Polymer 14 | 250 |

Example 42

To an aqueous solution in which the polymer 1 obtained in Preparation Example 1 is added at 50 ppm, sodium hydroxide was added to adjust the pH to 10. The bactericidal property test of this aqueous solution was carried out with contact time of 1 minute based on ASTM E-2315-03. The anti-bacterial activity value for *Escherichia coli* was 2.5, thus showing the bactericidal activity.

Similar to the above, to an aqueous solution in which the polymer 5 or 10 to 14 obtained in Preparation Example 1 was added at 50 ppm, sodium hydroxide was added to adjust the pH to 10. The bactericidal property test of this aqueous solution was carried out with contact time of 1 minute based on ASTM E-2315-03. The results are shown in Table 7. From Table 7, it is found that the polymers 5 and 10 to 14 can exhibit a high bactericidal effect for *Escherichia coli* and *Staphylococcus aureus* even with short contact time.

TABLE 7

| | Bactericidal activity value | |
|---|---|---|
| Antimicrobial agent | *Escherichia coli* | *Staphylococcus aureus* |
| Polymer 5 | 4.8 | 4.9 |
| Polymer 10 | 1.4 | 3.6 |
| Polymer 11 | 4.6 | >5.1 |
| Polymer 12 | 4.1 | >5.1 |
| Polymer 13 | 0.5 | 4.0 |
| Polymer 14 | 0.5 | 4.0 |

Examples 43 to 46 and Comparative Example 5

To an aqueous solution added with the polymer 1 which has been obtained in Preparation Example 1 and benzalkonium chloride at 0.1% by weight, various kinds of alkali modifying agent shown in Table 8 were mixed at 1% by weight to prepare an antimicrobial agent composition. A pH of each aqueous solution is shown in Table 8. The storage stability test was carried out for the antimicrobial agent compositions for 18 days at 55° C. Results of measuring the minimum growth inhibitory concentration (MIC) of the antimicrobial agent compositions after the storage stability test are shown in Table 8. Meanwhile, MIC values were described as concentration of the antimicrobial agent. As shown in Table 8, benzalkonium chloride as a conventionally used antimicrobial agent shows poor antimicrobial performance after the storage under alkali conditions. However, the polymer 1 was found to maintain the high antimicrobial performance.

TABLE 8

| | | | | MIC (ppm) | |
|---|---|---|---|---|---|
| | Antimicrobial agent | Alkali modifying agent | pH | *Escherichia coli* | *Staphylococcus aureus* |
| Example 43 | Polymer 1 | NaOH | 12.5 | 16 | 8 |
| Example 44 | Polymer 1 | Monoethanolamine | 10.9 | 16 | 8 |
| Example 45 | Polymer 1 | Sodium carbonate | 10.9 | 16 | 8 |
| Example 46 | Polymer 1 | Sodium citrate | 8.3 | 16 | 8 |
| Comparative Example 5 | Benzalkonium chloride | NaOH | 12.5 | 250 | 250 |

Examples 47

An anti-fungi test was carried out by using the polymer 1 which has been obtained in Preparation Example 1. The results are shown in Table 9.
[Chemical Formula 6]
○: Fungi growth was not observed at all.
Δ; Slight fungi growth was observed.
X: Fungi growth was observed from the entire plate surface.

TABLE 9

| Culture time | Presence or absence growth of fungi |
|---|---|
| For 3 days | ○ |
| For 1 week | Δ |

Antimicrobial Performance in Detergent Composition: Examples 48 to 52 and Comparative Examples 6 to 8

A composition with the composition described in Table 10 was prepared and the bactericidal performance test was carried out for the aqueous solution based on ASTM E2315-03. Herein, the contact time between a liquid of bacterial cells and an aqueous solution was 10 minutes, and the bactericidal activity value of 2 or more was expressed as ⊙, the bactericidal activity value of 1 or more but less than 2 was expressed as ⊙, and the bactericidal activity value of less than 1 was expressed as X. The results are shown in Table 10. As shown in Table 10, it was found that the polymer 11 can sufficiently exhibit the bactericidal effect even in the presence of an anionic surfactant, a non-ionic surfactant, or a cationic surfactant, which are usually included in a common detergent, or a polyanion which is used as a detergent builder.

Meanwhile, as a surfactant, hexadecyltrimethyl ammonium chloride (manufactured by Wako Pure Chemical Industries, Ltd.), polyoxyethylenelauryl ether (Emulgen 108, manufactured by Kao Corporation), sodium linear alkylbenzene sulfonate (manufactured by Wako Pure Chemical Industries, Ltd.), and fatty acid sodium of palm oil (manufactured by NOF CORPORATION) were used. Furthermore, as a detergent builder, acrylic acid/maleic acid copolymer salt (Aqualic (registered trade mark) L-TL, manufactured by Nippon Shokubai Co., Ltd.) was used.

adjusted to 105 CFU/mL was inoculated thereto followed by static culture for 18 hours at 37° C. To the vial bottle after culture, physiological saline (20 ml) containing 0.7% by weight polysorbate 80 and 0.1% by weight soy bean lecithin was added followed by shaking. Dilution series were prepared by the ten fold dilution method, and after inoculation by applying the cells to a Mueller-Hinton agar medium, the cells were cultured for 24 hours at 37° C. and the viable cell count was measured. A reduced cell count was expressed in terms of a logarithmic value that was obtained by subtracting a logarithmic value of cell count of the above-treated test cloth from a logarithmic value of cell count obtained by carrying out the same test as above with a cloth which was treated with water without containing any antimicrobial components. It is found that, when the reduced cell count expressed in terms of a logarithmic value is 1 or more, an antimicrobial property is exhibited and when it is 2 or more, a sufficient antimicrobial property is exhibited. A case in

TABLE 10

|  |  | Example | | | | | Comparative Example | | |
|---|---|---|---|---|---|---|---|---|---|
|  |  | 48 | 49 | 50 | 51 | 52 | 6 | 7 | 8 |
| Composition (ppm) | Polymer 11 | 10 | 10 | 10 | 10 | 10 |  |  |  |
|  | Hexadecyltrimethyl ammonium chloride |  | 5 |  | 5 | 5 | 10 | 5 | 5 |
|  | Polyoxyethylenelauryl ether |  |  | 100 | 100 | 100 | 100 | 100 | 100 |
|  | Sodium linear alkylbenzene sulfonate |  |  |  |  | 10 |  |  | 10 |
|  | fatty acid sodium of palm oil |  |  |  | 10 | 10 |  | 10 | 10 |
|  | Acrylic acid/maleic acid copolymer salt |  |  |  | 10 |  |  | 10 |  |
|  | Sterilized water |  |  |  | remnant |  |  |  |  |
| Evaluation | Bactericidal activity value | *Escherichia coli* | ⊙ | ⊙ | ○ | ⊙ | ○ | X | X | X |
|  |  | *Staphylococcus aureus* | ⊙ | ⊙ | ⊙ | ○ | ○ | X | X | X |

Adsorption Persistence for Cotton Cloth: Examples 53 to 56 and Comparative Examples 9 to 11

A cotton cloth (Kanakin #3, Japanese Standards Association) was cut to 0.4 g each, sterilized in a vial bottle, and dried. Next, the sterilized and dried cloth was impregnated for 30 minutes in 5 ml of an aqueous solution with the composition shown in Table 11. Meanwhile, for the polymers 17 and 18, an aqueous solution was prepared by using 1% by weight aqueous solution of each polymer which has been prepared in the above. The impregnated cloth was sandwiched between clean paper towels, and then dehydrated by applying pressure. Subsequently, it was subjected to rinsing and dehydration, 3 times for each. For the rinsing and dehydration, the cloth was stirred (rinsed) in a beaker added with 20 ml of ultrapure water, sandwiched between paper towels, and dehydrated by applying pressure. After 3 times of the rinsing and dehydration, the cloth was separately added to a vial bottle, that is, one piece per vial, and then dried overnight. The resultant was employed as a test cloth.

The antimicrobial property test of a test cloth was carried out based on JIS L1902:2008. The test cloth which has been treated in the above was added to a vial bottle, and 0.2 ml of a bacterial suspension of *Escherichia coli* or *Staphylococcus aureus* of which bacterial cell count has been which the reduced cell count expressed in terms of a logarithmic value is 2 or more is labeled as ⊙, a case in which the reduced cell count expressed in terms of a logarithmic value is 1 or more and less than 2 is labeled as ○, and a case in which the reduced cell count expressed in terms of a logarithmic value is less than 1 is labeled as X. The results are shown in Table 11. As shown in Table 11, when the polymer 5, 10, or 11 is used, the test cloth exhibited an effective antimicrobial property even after repeated rinsing and dehydration, representing an excellent adsorption retention property for test cloth. Furthermore, as shown in Table 11, even after rinsing and dehydration in the presence of an anionic surfactant, a non-ionic surfactant, or a cationic surfactant, which are usually included in a common detergent, or a polyanion which is used as a detergent builder, the test cloth exhibited an effective antimicrobial property, and thus an excellent adsorption retention property for cloth was shown with the polymer 10 compared to the polymers 17 to 19.

Meanwhile, as a surfactant, hexadecyltrimethyl ammonium chloride (manufactured by Wako Pure Chemical Industries, Ltd.), polyoxyethylenelauryl ether (Emulgen 108, manufactured by Kao Corporation), sodium linear alkylbenzene sulfonate (manufactured by Wako Pure Chemical Industries, Ltd.), and fatty acid sodium of palm oil (manufactured by NOF CORPORATION) were used.

TABLE 11

|  |  | Example | | | | Comparative Example | | |
| --- | --- | --- | --- | --- | --- | --- | --- | --- |
|  |  | 53 | 54 | 55 | 56 | 9 | 10 | 11 |
| Composition (ppm) | Polymer 10 | 10 |  |  | 10 |  |  |  |
|  | Polymer 11 |  | 10 |  |  |  |  |  |
|  | Polymer 5 |  |  | 10 |  |  |  |  |
|  | Polymer 17 |  |  |  |  | 10 |  |  |
|  | Polymer 18 |  |  |  |  |  | 10 |  |
|  | Polymer 19 |  |  |  |  |  |  | 10 |
|  | Hexadecyltrimethyl ammonium chloride |  |  |  | 5 | 5 | 5 | 5 |
|  | Polyoxyethylenelauryl ether |  |  |  | 100 | 100 | 100 | 100 |
|  | Sodium linear alkylbenzene sulfonate |  |  |  | 10 | 10 | 10 | 10 |
|  | fatty acid sodium of palm oil |  |  |  | 10 | 10 | 10 | 10 |
|  | Sterilized water |  |  |  | remnant |  |  |  |
| Evaluation | Bactericidal activity value | *Escherichia coli* | ⊙ | ⊙ | ⊙ | ⊙ | X | X | X |
|  |  | *Staphylococcus aureus* | ⊙ | ⊙ | ⊙ | ○ | X | X | X |

Adsorption Persistence for Hair: Examples 57 to 59 and Comparative Examples 12 to 14

Antimicrobial Performance Against Dandruff-Causing Bacteria

To CHROMagar *Malassezia* medium (manufactured by Kanto Chemical Co., Inc.), *Malassezia furfur* (NBRC-0656) said to be dandruff-causing fungus was inoculated and subjected to static culture for 72 hours at 30° C. The appeared colonies were scraped and suspended in a Butterfield's buffer solution so as to prepare a liquid of fungal cells of $10^6$ CFU/mL. To a test tube, 4 ml of 103 medium (1.0% by weight of glucose, 0.5% by weight of peptone, 0.3% by weight of yeast extract, 0.3% by weight of malt extract, and 1.0% by weight of olive oil, all dissolved in sterilized water to have the described concentration), 0.5 ml of a test chemical in which the polymer shown in Table 12 was diluted by distilled water to have final concentration of 10 ppm (meanwhile, for the polymers 17 and 18, 1% by weight aqueous solution which has been prepared in the above was used), and 0.5 ml of the prepared liquid of *Malassezia furfur* were added and mixed therein. After that, shaking culture was performed for 72 hours at 30° C. Cell proliferation state was then observed. If no cell growth was observed, it was labeled as ○, and if cell growth was observed, it was labeled as X. The results are shown in Table 12.

As shown in Table 12, it was found that the polymer 5, 10, and 11 have excellent antimicrobial performance against *Malassezia furfur* when compared to the polymers 17 to 19.

Hair Remaining Ratio 1 g of human hair tresses was washed 2 times with 15 ml of methanol followed by drying. The hair tresses were added to a 110 ml screw vial (manufactured by AS ONE Corporation, No. 8), and 0.1% solution of the polymer shown in Table 12 was added in an amount of 10 g followed by shaking by hands for 30 seconds. Meanwhile, for the polymers 17 to 19, the 1% by weight aqueous solution prepared in the above was used. By using a pipette, the polymer solution was transferred to another container, and the hair tresses were washed 2 times with 10 g of water at 40° C. Then, the hair tresses were dried naturally. The amount of the polymer remaining in the dried hair tresses was quantified by carrying out extraction 2 times with 15 ml of methanol, and carrying out colloid titration of the amine amount in the extract by using 1/400 N potassium polyvinyl sulfate solution and toluidine blue as an indicator. In Table 12, the hair remaining ratio calculated based on the following formula was indicated. As shown in Table 12, compared to the polymers 17 to 19, the remaining ratio was 2 time or more with the polymer 5, 10, and 11 which have the structure of the present invention. Furthermore, as there was an antimicrobial property against *Malassezia furfur* as a dandruff-causing bacterium, it was found that dandruff can be sufficiently prevented even for hair after hair washing.

[Mathematical Formula 3]

$$\text{Hair remaining ratio (\%)} = \frac{\text{Amount of } N \text{ in extract (mol)}}{\text{Amount of } N \text{ in 10 g of 0.1\% aqueous solution (mol)}} \times 100$$

TABLE 12

|  | Example | | | Comparative Example | | |
| --- | --- | --- | --- | --- | --- | --- |
|  | 57 | 58 | 59 | 12 | 13 | 14 |
|  | Polymer 5 | Polymer 10 | Polymer 11 | Polymer 17 | Polymer 18 | Polymer 19 |
| Antimicrobial performance against *Malassezia furfur* | ○ | ○ | ○ | ○ | X | X |
| Hair remaining ratio (%) | 20 | 15 | 26 | 6 | 7 | 5 |

Adsorption Persistence for Skin: Examples 60 to 62 and Comparative Examples 15 to 17

Antimicrobial Performance Against Bacteria for Causing Armpit Odor

To TSB agar medium (1.7% by weight of casein peptone, 0.3% by weight soy peptone, 0.5% by weight of sodium chloride, 0.25% by weight of dipotassium phosphate, 0.25% by weight of glucose, and 1.8% by weight of agar, all dissolved in sterilized water to have the described concentration), *Corynebacterium* xerosis (NBRC-16721) which is said to be one of the bacteria for causing armpit odor was inoculated and subjected to pre-culture for 2 days at 37° C.

The appeared colonies were scraped and suspended in a Butterfield's buffer solution so as to prepare a liquid of bacterial cells of 107 CFU/mL. To 4 ml of a Butterfield's buffer solution, 0.5 ml of a test chemical in which the polymer shown in Table 13 is diluted by distilled water to have final concentration of 10 ppm (meanwhile, for the polymers 17 and 18, 1% by weight aqueous solution which has been prepared in the above was used), and 0.5 ml of the prepared liquid of Corynebacterium xerosis were added and slowly stirred using a mild shaker for 30 minutes at 25° C. To 5 ml of the liquid after stirring, physiological saline (5 ml) containing 0.7% by weight polysorbate 80 and 0.1% by weight soy bean lecithin was added followed by stirring. Next, dilution series were prepared by the ten fold dilution method, and after inoculation by applying the cells to a TSB agar medium, the cells were cultured for 48 hours at 30° C. and the viable cell count was measured. A logarithm of the above measured viable cell count was subtracted from a logarithm of the control (in which sterilized water is used instead of test chemical) cell count, and the result is used as antimicrobial activity. When the antimicrobial activity is 1 or more, it is found to have an antimicrobial activity. When it is 2 or more, it is found to have a sufficient antimicrobial activity. Furthermore, when the antimicrobial activity value is 2 or more in terms of a logarithmic value, it is labeled as ○. When it is 1 or more and less than 2, it is labeled as Δ, and when it is less than 1, it is labeled as X. The results are shown in Table 13. As shown in Table 13, it was found that the polymers 5, 10, and 11 have excellent antimicrobial performance against Corynebacterium xerosis when compared to the polymers 17 to 19.

Aldehyde Adsorbing Performance

A container added with 0.5 g of the polymer shown in Table 13 was placed in a smart bag PA (AKK-3, manufactured by GL Sciences Inc.) followed by heat sealing for tight closing. The smart bag PA was prepared to be in vacuum state, and then added with nitrogen. 0.5 μL of 10% by weight ethanol solution of nonenal (Tokyo Chemical Industry Co., Ltd.) or 5 ml of diacetyl (gas) (manufactured by Tokyo Chemical Industry Co., Ltd.) was added thereto by using a syringe. After 2 hours, the gas concentration was measured using a gas detecting tube (for nonenal, gas detecting tube for formaldehyde, and for diacetyl, gas detecting tube for acetaldehyde). Based on the following formula, the adsorption rate of nonenal and diacetyl was calculated. When the adsorption rate is 90% or more, it is labeled as ○. When the adsorption rate is 80% or more, it is labeled as Δ, and when the adsorption rate is less than 80%, it is labeled as X. The results are shown in Table 13. As shown in Table 13, because the polymers 5, 10, and 11 have excellent aldehyde adsorbing property and also have antimicrobial property against Corynebacterium xerosis, it was shown that they are an antimicrobial agent which has both effects of suppressing an occurrence of armpit odor and having a deodorant effect even in case of having an occurrence of armpit odor.

[Mathematical Formula 4]

$$\text{Adsorption ratio (\%)} = \frac{\text{Gas concentration of blank} - \text{Gas concentration with addition of the polymer}}{\text{Gas concentration of blank}} \times 100$$

Adsorption Persistence for Skin

Inside of a forearm was cleaned with ethanol, and on a test area (width×length=3 cm×3 cm), 0.1 g of 1% by weight aqueous solution of the polymer described in Table 13 was applied followed by natural drying. After 7 hours, the mouth of a sample bottle (Laboran screw vial bottle No. 4) added with 10 ml of methanol was pressed against the test area and washing was carried out 3 times. The washout solutions were all mixed, and the amount of N in the washout solution was quantified by colloid titration using $\frac{1}{400}$ N potassium polyvinyl sulfate solution. In Table 13, the skin remaining ratio calculated based on the following formula is described. As shown in Table 13, the polymers 5, 10, and 11 with the structure of the present invention have higher skin remaining ratio compared to the polymers 17 to 19.

[Mathematical Formula 5]

$$\text{Skin remaining ratio (\%)} = \frac{\text{Amount of } N \text{ in extract (mol)}}{\text{Amount of } N \text{ in 0.1 g of 1\% aqueous solution (mol)}} \times 100$$

TABLE 13

| | | Example | | | Comparative Example | | |
|---|---|---|---|---|---|---|---|
| | | 60 Polymer 5 | 61 Polymer 10 | 62 Polymer 11 | 15 Polymer 17 | 16 Polymer 18 | 17 Polymer 19 |
| Antimicrobial performance against Corynebacterium xerosis | | ○ | ○ | ○ | X | Δ | X |
| Aldehyde adsorbing performance | Nonenal | ○ | ○ | ○ | Δ | Δ | X |
| | Diacetyl | ○ | ○ | ○ | Δ | Δ | X |
| Skin remaining ratio (%) | | 6.2 | 7.0 | 6.5 | 3.2 | 2.8 | 1.1 |

Antimicrobial Performance Under Acidic and Neutral Conditions: Examples 63 to 65

The minimum growth inhibitory concentration (MIC) was measured for 20% by weight aqueous solution of the polymer 5, 11, 12 of which pH has been adjusted to pH 5 and pH 7 by using hydrochloric acid. The results are shown in Table 14. As shown in Table 14, the polymer of the present invention can exhibit the antimicrobial performance at acidic conditions and also at neutral conditions.

TABLE 14

| | Antimicrobial agent | MIC (ppm) | | | | | |
| --- | --- | --- | --- | --- | --- | --- | --- |
| | | pH = 5 | | | pH = 7 | | |
| | | *Escherichia coli* | *Staphylococcus aureus* | *Pseudomonas aeruginosa* | *Escherichia coli* | *Staphylococcus aureus* | *Pseudomonas aeruginosa* |
| Example 63 | Polymer 5 | 13 | 6 | 4 | 13 | 6 | 6 |
| Example 64 | Polymer 11 | 13 | 4 | 4 | 13 | 4 | 4 |
| Example 65 | Polymer 12 | 25 | 8 | 25 | 25 | 8 | 50 |

The antimicrobial agent using the polyalkyleneimine derivative of the present invention can be used for cleaning agent application like a laundry cleaning agent, a softening agent, a dishwashing agent, and an agent for cleaning hard surfaces; personal care application like shampoo, rinse, a cosmetic product, and an antiperspirant; and industrial applications like paint, a wood preservative, a cement admixture, and industrial water (for example, water for paper making step in paper-manufacturing process, cooling water or cleaning water for various industrial uses).

The present application is based on the Japanese patent application No. 2014-184692 filed on Sep. 10, 2014, Japanese patent application No. 2014-247311 filed on Dec. 5, 2014, and Japanese patent application No. 2015-049989 filed on Mar. 12, 2015. The disclosed contents thereof are referred to and incorporated herein as a whole.

The invention claimed is:

1. An antimicrobial agent comprising a polyalkyleneimine derivative formed by directly adding a substituent group having a structure of a following Formula (1) to a nitrogen atom of polyalkyleneimine:

[Chemical Formula 1]

$$—CH_2CH(OH)CH_2—O—R^1 \quad (1)$$

in the formula, $R^1$ represents an alkyl group with 6 to 20 carbon atoms, an alkenyl group with 6 to 20 carbon atoms, an aryl group with 6 to 20 carbon atoms, or $—(CH_2CH_2O)_n—R^2$, in which $R^2$ represents an alkyl group with 6 to 20 carbon atoms, an alkenyl group with 6 to 20 carbon atoms, or an aryl group with 6 to 20 carbon atoms; and n represents an integer of 1 to 50, wherein a weight average molecular weight of the polyalkyleneimine derivative is 3000 Da or lower.

2. The antimicrobial agent according to claim 1, wherein the weight average molecular weight of the polyalkyleneimine derivative is 400 Da to 3,000 Da.

3. The antimicrobial agent according to claim 1, wherein the polyalkyleneimine is polyethyleneimine.

4. The antimicrobial agent according to claim 1, further comprising an anionic surfactant.

5. The antimicrobial agent according to claim 1, further comprising an alkali modifying agent.

6. A personal care product, a product for caring household goods, or a skin care product comprising the antimicrobial agent according to claim 1.

* * * * *